(12) United States Patent
Dobrilovic

(10) Patent No.: US 10,987,222 B2
(45) Date of Patent: Apr. 27, 2021

(54) HEART VALVE SIZING RING AND METHOD

(71) Applicant: Nikola Dobrilovic, Boston, MA (US)

(72) Inventor: Nikola Dobrilovic, Boston, MA (US)

( * ) Notice: Subject to any disclaimer, the term of this patent is extended or adjusted under 35 U.S.C. 154(b) by 87 days.

(21) Appl. No.: 16/297,926

(22) Filed: Mar. 11, 2019

(65) Prior Publication Data

US 2019/0201202 A1 Jul. 4, 2019

Related U.S. Application Data

(63) Continuation of application No. 15/839,441, filed on Dec. 12, 2017, now Pat. No. 10,271,952, which is a continuation of application No. 13/658,050, filed on Oct. 23, 2012, now Pat. No. 9,889,009.

(60) Provisional application No. 61/555,002, filed on Nov. 3, 2011, provisional application No. 61/551,728, filed on Oct. 26, 2011.

(51) Int. Cl.
*A61F 2/24* (2006.01)
*A61B 17/04* (2006.01)
*A61B 17/02* (2006.01)
*A61B 17/00* (2006.01)

(52) U.S. Cl.
CPC ........ *A61F 2/2496* (2013.01); *A61B 17/0483* (2013.01); *A61B 17/0293* (2013.01); *A61B 2017/00725* (2013.01); *A61F 2/2448* (2013.01)

(58) Field of Classification Search
CPC .................................. A61F 2/24; A61B 17/04
See application file for complete search history.

(56) References Cited

U.S. PATENT DOCUMENTS

| | | | |
|---|---|---|---|
| 5,071,431 A | 12/1991 | Sauter et al. |
| 5,360,014 A | 11/1994 | Sauter et al. |
| 5,489,296 A | 2/1996 | Love et al. |
| 5,669,919 A | 9/1997 | Sanders et al. |
| 5,814,096 A | 9/1998 | Lam et al. |
| 5,843,177 A | 12/1998 | Vanney et al. |
| 6,019,739 A | 2/2000 | Rhee et al. |
| 6,110,200 A | 8/2000 | Hinnenkamp |
| 6,458,155 B1 | 10/2002 | Van Nguyen et al. |
| 6,678,962 B1 | 1/2004 | Love et al. |
| 6,702,763 B2 | 3/2004 | Murphy et al. |

(Continued)

FOREIGN PATENT DOCUMENTS

| JP | 11206739 A | 8/1999 |
|---|---|---|
| WO | 2012019052 A2 | 2/2012 |

OTHER PUBLICATIONS

Peters Surgical, "uniRing Universal Annuloplasty System", 2007 http://www.zenomedical.com/Images/Products/Brochures/uniRing.pdf.

*Primary Examiner* — Matthew W Schall
(74) *Attorney, Agent, or Firm* — Barlow, Josephs & Holmes, Ltd.

(57) ABSTRACT

A device for measuring heart valve for sizing a heart valve reinforcement ring, includes a first handle having a first shaft an outer ring coupled to the first shaft, wherein the outer ring has an inner surface; and an inner ring having an outer surface, wherein the inner ring is removably couplable to the outer ring. The inner surface of the outer ring and the outer surface of the inner ring further have reciprocal mating surfaces configured and arranged to grip sutures therebetween when coupled together. The device may further have a second handle with a second shaft connected to the inner ring. Alternatively, the first handle may have a second shaft that is connected to a second outer ring.

17 Claims, 7 Drawing Sheets

(56) References Cited

U.S. PATENT DOCUMENTS

| | | |
|---|---|---|
| 6,719,785 B2 | 4/2004 | Schoon et al. |
| 7,338,484 B2 | 3/2008 | Schoon et al. |
| 2002/0129820 A1 | 9/2002 | Ryan et al. |
| 2003/0069593 A1 | 4/2003 | Tremulis et al. |
| 2008/0033544 A1 | 2/2008 | Lemmon |
| 2009/0093877 A1 | 4/2009 | Keider et al. |
| 2009/0210051 A1 | 8/2009 | Camedda et al. |
| 2010/0030329 A1 | 2/2010 | Frater |
| 2010/0152844 A1 | 6/2010 | Couetil |
| 2010/0262043 A1 | 10/2010 | Sauter et al. |
| 2012/0071968 A1 | 3/2012 | Li et al. |

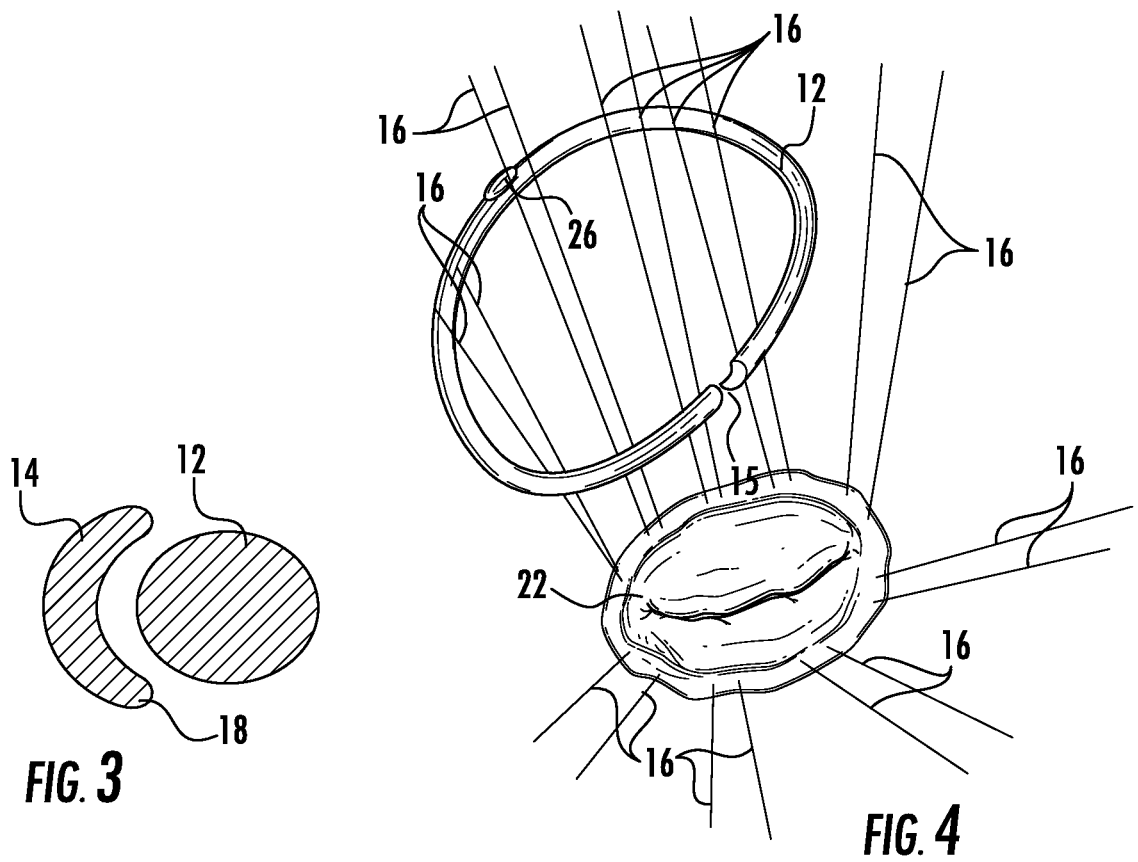
FIG. 3
FIG. 4
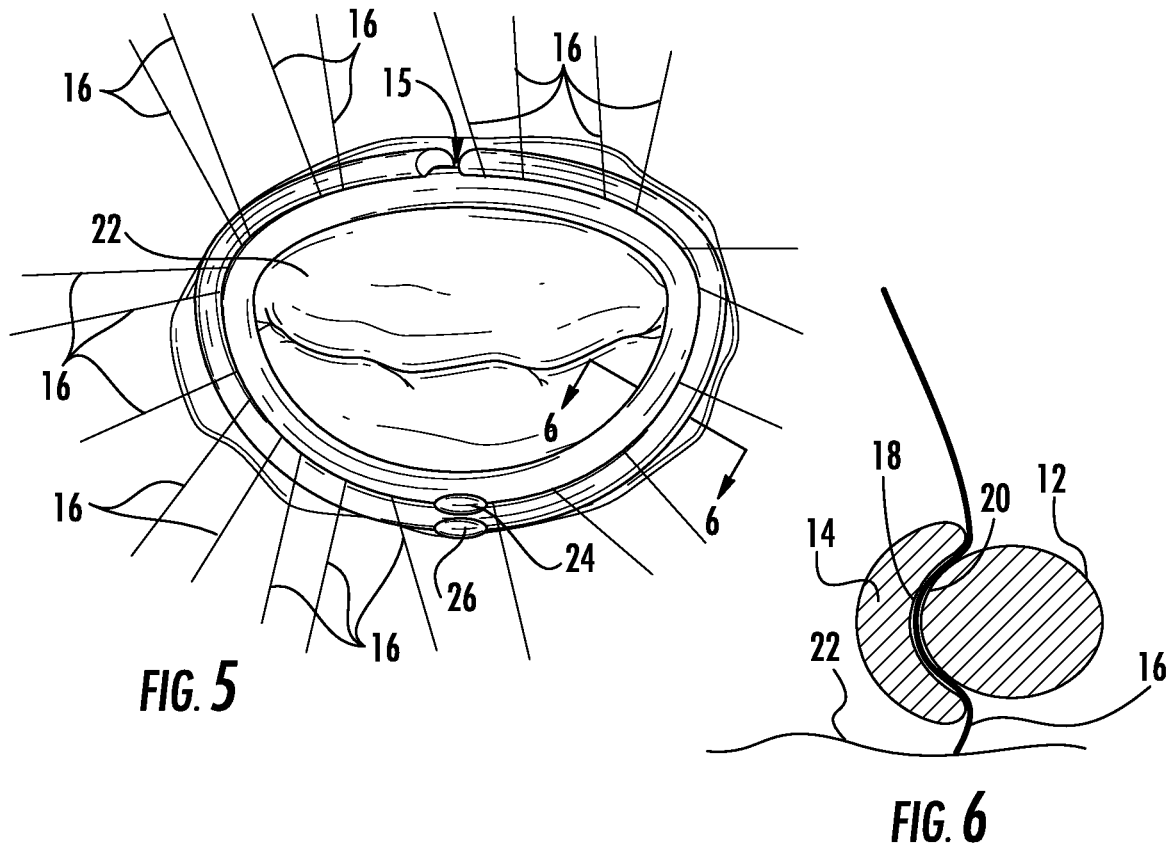
FIG. 5
FIG. 6

HEART VALVE SIZING RING AND METHOD

CROSS-REFERENCE TO RELATED APPLICATIONS

This patent document is a continuation of earlier filed U.S. Non-Provisional application Ser. No. 15/839,441, filed on Dec. 12, 2017, which is a continuation of U.S. Non-Provisional application Ser. No. 13/658,050, filed on Oct. 23, 2012, which claims priority to U.S. Provisional Application Ser. No. 61/551,728, filed on Oct. 26, 2011, and U.S. Provisional Application Ser. No. 61/555,002, filed on Nov. 3, 2011, the entire contents of which are incorporated herein by reference.

BACKGROUND

1. Technical Field

The present patent document relates generally to heart valve repair in open heart surgery and more specifically to a heart valve sizing ring and method to properly size a heart valve reinforcement ring prosthesis for proper implantation.

2. Background of the Related Art

Accurate selection of ring size and shape is a critical component of heart valve repair surgery. Current "annulus-sizers" or "valve-sizers" are, by design, not very accurate at actually assessing size (they only provide an estimate) and, certainly, provide no ability for physiologic assessment of the repair procedure in terms of valve function after repair.

Therefore, there is a perceived need in the industry for a ring sizing tool that allows the surgeon to accurately assess the size of the ring prosthesis needed and allows assessment of the fit on the patient, i.e. whether the fit is leaky or too tight.

SUMMARY

The present invention solves the problems of the prior art by providing a ring sizing tool that includes an outer ring portion with small gap formed therethrough and an inner mating surface on the interior portion of the ring. An inner ring is sized to snap fit into the outer ring and includes a reciprocal mating surface designed to engage the inner mating surface of the outer ring yet prevent damage to sutures. The reciprocal surface preferably includes an outwardly deflected portion to direct sutures away from the heart valve.

BRIEF DESCRIPTION OF THE DRAWINGS

These and other features, aspects, and advantages of the present invention will become better understood with reference to the following description, appended claims, and accompanying drawings where:

FIG. 3 is a cross-section view through line 3-3 of FIG. 2;

FIG. 4 is a perspective view of the sutures being gathered within the outer ring an embodiment of a heart valve ring sizing tool of the present invention;

FIG. 5 is a perspective view showing of an embodiment of a heart valve ring sizing tool of the present invention in place over a heart valve with the sutures trapped between the outer and inner rings;

FIG. 6 is a cross-section view through line 6-6 of FIG. 5;

DESCRIPTION OF THE PREFERRED EMBODIMENT

Figure 1:
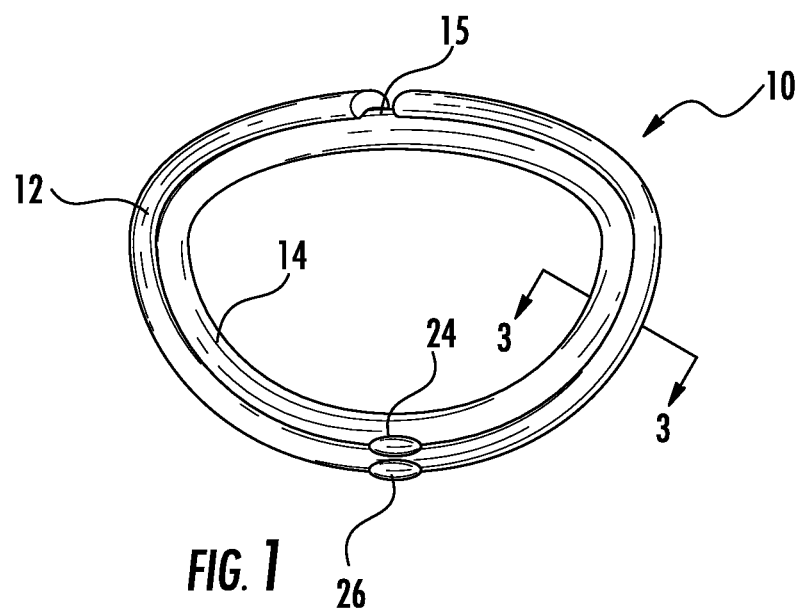
FIG. 1 is a perspective view of an embodiment of a heart valve ring sizing tool of the present invention.

The present invention is described generally for mitral heart valve repair surgery. But it is to be understood that the present invention may be adapted for use on tricuspid valve repair and aortic root/annulus remodeling procedures (such as Tirone David type-operations) where the present invention may be used to simulate down-sizing the aortic root as would be created by tube graft material.

The proposed device will: 1) provide a quick, more realistic, useful, functional, true-measurement of mitral annulus size, and 2) allow for critical physiologic assessment of valve function (and consequently the repair quality) prior to final and permanent ring selection and allow for such physiologic measurement and assessment using several different ring sizes and/or different ring models and shapes.

The key to proper/improved ring selection is not "just guessing" after estimation of size and shape based on examination/measurement of visualized anatomy but on the potential information gained from assessment of actual physiologic consequences secondary to ring implantation. The proposed device will allow for a quick assessment of the valve annulus/repair with the ability to then again quickly assess the same repair with a different sized or shaped device representing a corresponding different sized/shaped ring prior to final selection.

A key feature of this device is that an evaluation of valve physiology (i.e. testing a particular size and shape ring on the valve) can be obtained prior to commitment to a particular ring, which, under normal circumstances, is then (permanently) sewn into position. Currently, it is only after the ring is sewn into position, that the valve's repair status can be optimally assessed intraoperatively.

The principal design would feature a device which quickly "captures" and aligns the ring sutures after they have been placed in the mitral valve annulus and after any complex repair had been completed such as quadrangular resection, etc. The alignment/positioning of the ring sutures would be such that the annulus size and shape, corresponding to a particular ring, would be essentially reproduced for the purpose of a quick, accurate assessment of function of the new post-repair physiology, degree of leaflet coaptation, etc. The device could be quickly exchanged for another similar device which represents the different size and/or shape of another ring. If several such measurements can be executed efficiently and safely, the surgeon will be much more informed and secure in his decision regarding ring selection as it will be based, at least to a significant degree, on actual measurement and more importantly on actual physiologic assessment.

It is the hope that such preliminary physiologic assessment will translate into the best final outcome for the patient. The added information provided by quick and more accurate assessment of valve function, as described above, has the potential to significantly diminish the dreaded consequence of having to entirely remove and replace a poorly functioning valve ring/repair after separation from bypass and realization that the valve repair is functioning sub-optimally (or that a sub-optimal repair is left in place and "accepted" even though the surgeon is clearly unhappy with the suboptimal result). "Undersizing" of the annulus can also be better avoided and thus reduce the incidence of the unfavorable complication of "SAM" (systolic anterior motion) or having suboptimal hemodynamics from a smaller valve orifice or ring prosthesis shape.

Figure 2:
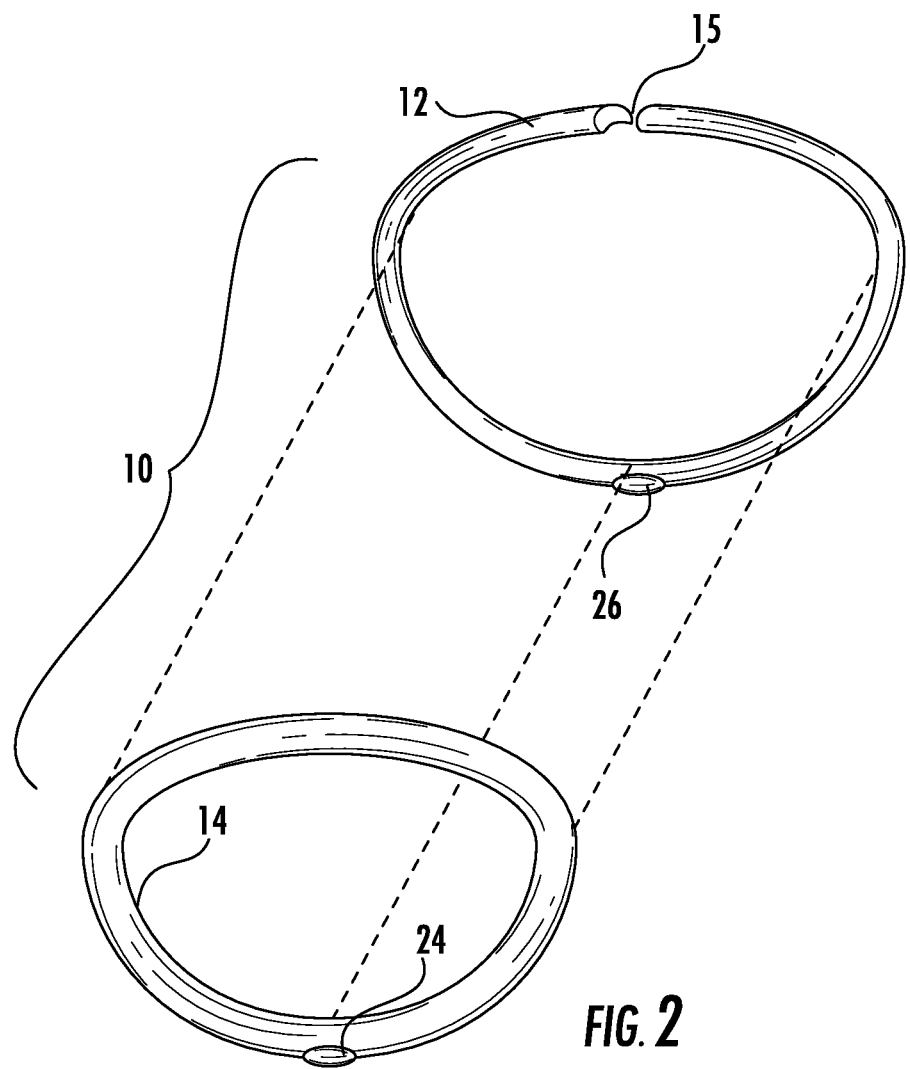
FIG. 2 is an exploded view of an embodiment of a heart valve ring sizing tool of the present invention.

The described functions of this device can be achieved in a variety of ways. Referring now to FIGS. 1-2, a first embodiment 10 of the heart valve sizing tool of the present invention includes two rings 12, 14 which "snap" together. The outer ring 12 could be incomplete, having a small gap 15, to allow it to be used to gather all of the annular sutures within the outer ring 12 in a quick and easy manner (as shown in FIG. 4). The inner ring 14 would be complete and would "snap" into the slightly larger outer ring 14. In doing so, the two rings 12, 14 would firmly, yet without damage to suture material, capture all sutures 16 in between the two rings 12, 14 (best seen in FIGS. 5 and 6). The device could then be "seated" into position (at annular level) in a fashion that mimics the function of a particular ring.

The inner ring 14 preferably includes a concave surface 18 on the outer portion of the ring 14. The outer ring 12 preferably includes a complimentary convex surface 20 on the inner portion of the ring 12. The concave and convex surfaces 18, 20 couple together to hold the rings 12, 14 in an assembled state as shown in FIG. 3. Because the inner ring 14 includes a concave surface 18 and the outer ring 12 includes a convex surface 20, the sutures 16, when captured between the rings 12,14, are deflected outwards and away from the heart valve 22 permitting assessment of the physiology by being able to better view the fit.

The inner ring 14 and outer ring 12 may each optionally include a tab 24, 26, respectively, extending from a portion of the ring 12, 14, preferably the bottom portion, to enable forceps to position and pull apart the two rings 12, 14. The tabs 24, 26 may be angled away from the center of the rings 12, 14 for easier gripping and manipulation.

Each particular device would correspond to a particular ring product of specified size and shape reproducing anticipated valve physiology should that particular ring size/shape be selected. The valve repair could be "tested" in standard fashion by "pressurizing" with saline, by examination, and/ or by other techniques. When ring function is reproduced in this manner, leaflet coaptation, as well as success of repair techniques, can be evaluated and compared at various ring sizes/shapes prior to final selection of the optimal, simply by swapping out the sizing device for one of different size/ shape. Several different ring sizes(/shapes) could be quickly swapped in and out for evaluation allowing for an informed, objective decision to be made. The device could be made of a variety of materials. Standard considerations would of course apply such as cost, bioreactivity, etc.

Ideally the device would be composed of a material which would not harm/damage/weaken/fray sutures. One such example of the device would be two hard (metal, plastic, etc.) rings with a soft rubber-like outer layer on each. The metal, or other similar firm material, would provide support and accuracy in size and shape, while the outer rubber, or similar material with resilient properties, layer would not only protect, but also, delicately, yet firmly, "grasp" the sutures between the two rings. Ideally, the "grip" on the sutures would be such that device would not slip over the sutures passively but could actively be slid by the surgeon across the sutures to allow for seating into the desired position up against the valve annulus.

In one embodiment of the heart valve sizing tool would be "stiff" to approximate the function of a "stiff" ring (possibly metal, plastic, etc). Though, other versions may exist to best approximate the physiologic support provided by various other types of rings (soft, partial, etc.). Ideally each size and variety/shape of mitral ring might have its own version of a sizing device. Optionally, to facilitate ring separation, small tabs (or similar structures) could be attached to each ring. The device may also be constructed in one of several other forms all of which achieve the previously stated general goals, but possibly with certain advantages or features.

Figure 7:
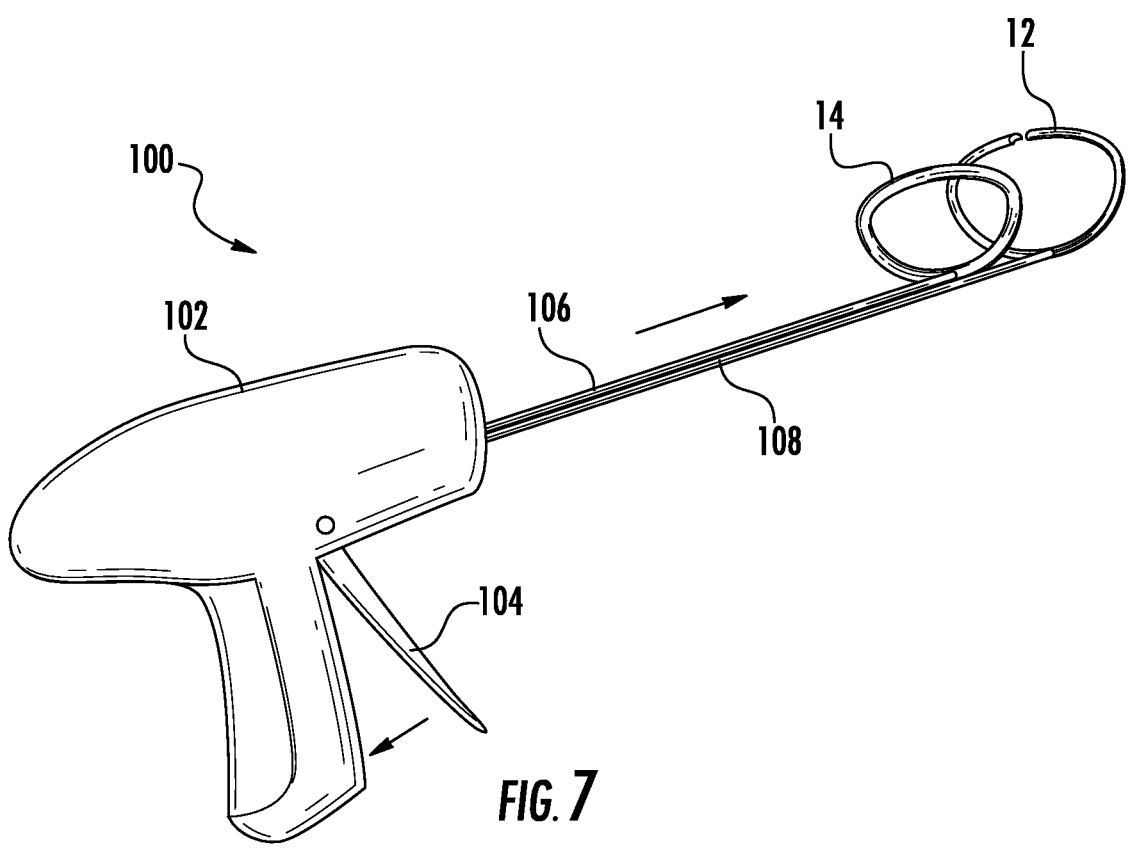
FIG. 7 is a perspective view of an alternative embodiment of the heart valve ring sizing tool of the present invention with the rings separated.
Figure 8:
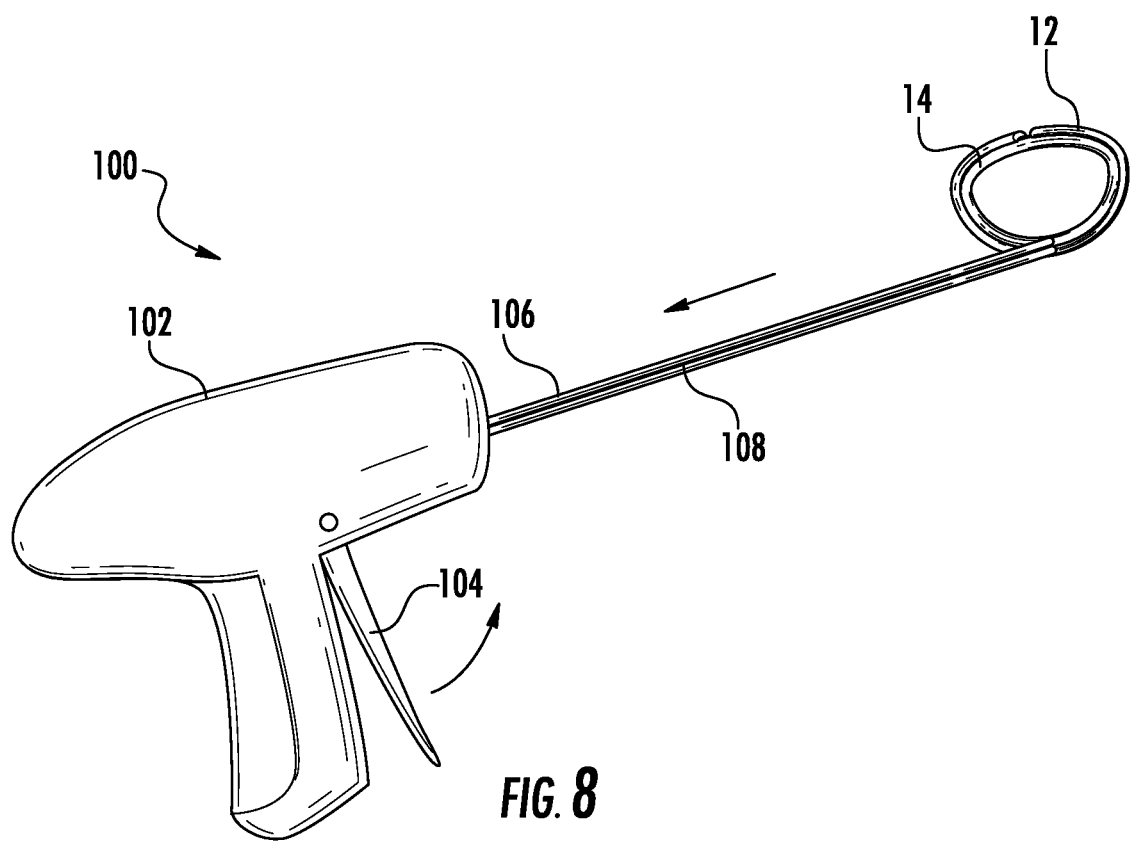
FIG. 8 is a perspective view of an alternative embodiment of the heart valve ring sizing tool of the present invention with the rings locked together.

Another embodiment of the device could be a solid "double-ring" design as one single (connected) unit. The inner ring would be solid 360 degrees, while the outer ring would be near 360 degrees (with a small access slit for example). This would allow the surgeon to gather all sutures with a single 360 degree "twirl" motion of the device. Once all sutures had been captured, the device could be pushed up against the mitral annulus (with some tension on the sutures). Variations on this particular design may include some form of mechanism which actively secures the sutures between the two rings by opposing one ring closely to the other after the sutures had been gathered. Examples could include, but are not limited to: one ring sliding (down the handle, as shown in FIGS. 7 and 8) onto the other ring, +/−locking down onto the other ring. Such functions may be operated by various mechanisms, including but not limited to, twisting mechanism which tightens one ring against the other, a sliding +/−locking mechanism which could be operated, for example, by the surgeon's thumb and two fingers (similar motion as for a syringe).

In another embodiment 100, a the heart valve sizing tool includes a handle 102 (best seen in FIGS. 7 and 8), similar to those used for valves/rings and may be useful with seating the device up against the annulus as well as facilitate other motions such as gathering sutures. A handle for the device could take one of several forms. The handle could be flexible, bendable, detachable (for example FIGS. 11 and 12 the handle may be removed from the heart valve sizing tool), etc. The handle 102 could facilitate manipulation and handling of the device. It would ideally provide optimal visualization of the valve leaflets for inspection as well as "testing" for leakage. The handle 102 could include a trigger 104 to force the inner ring 14 into position within the outer ring 12 once the sutures 16 are gathered within the outer ring 12. Pulling the trigger 104 pushes a shaft 106, which has the inner ring 14 attached on an end thereof. The outer ring 12 is attached to a second shaft 108 in a fixed position. Full deflection of the trigger 104 aligns the inner ring 14 within the outer ring 12. The inner and outer ring 12, 14 of a particular size may be exchanged from the handle 102 to the desired size.

Figure 9:
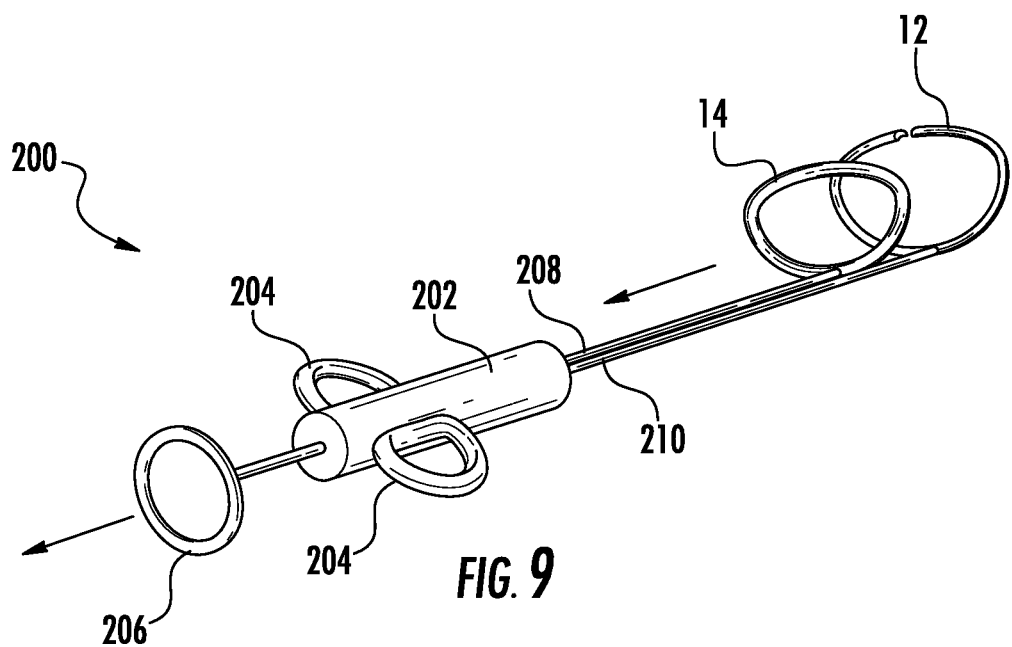
FIG. 9 is a perspective view of a second alternative embodiment of the heart valve ring sizing tool of the present invention with the rings separated.
Figure 10:
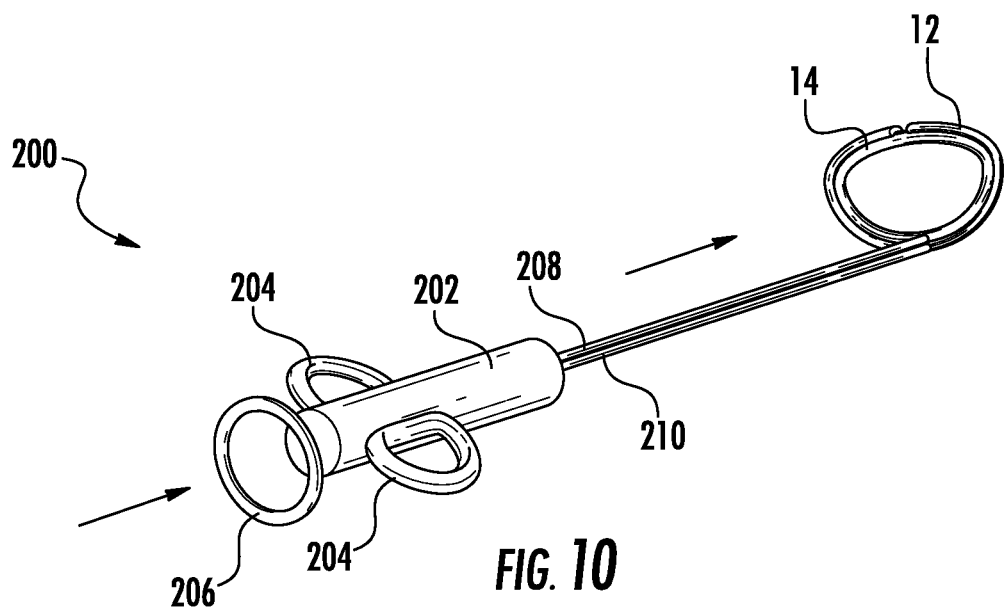
FIG. 10 is a perspective view of a second alternative embodiment of the heart valve ring sizing tool of the present invention with the rings locked together.

In a second alternative embodiment 200, a heart valve sizing tool includes a syringe-type handle 202 (best seen in FIGS. 9 and 10). A syringe-type handle 202 for the device could take one of several forms. The syringe-type handle 202 would be flexible, bendable, detachable, etc. The syringe-type handle 202 could facilitate manipulation and handling of the device. It would ideally provide optimal visualization of the valve leaflets for inspection as well as "testing" for leakage. The syringe-type handle 202 includes a pair of rings 204 to support the device on the surgeon's index and ring fingers. A device is operated with via the surgeon's thumb. A thumb ring 206, attached to a shaft 208, forces the inner ring 14 into position within the outer ring 12 once the sutures are gathered within the outer ring 12. Pushing the thumb ring 206 pushes the shaft 208, which has the inner ring 14 attached on an end thereof. The outer ring 12 is attached to a second shaft 210 in a fixed position. Fully depressing the thumb ring 206 aligns the inner ring 14 within the outer ring 12. The inner and outer ring 12, 14 of a particular size may be exchanged from the handle 202 to the desired size. Pulling on the thumb ring 206 separates the inner ring 14 from the outer ring 12.

Figure 11:
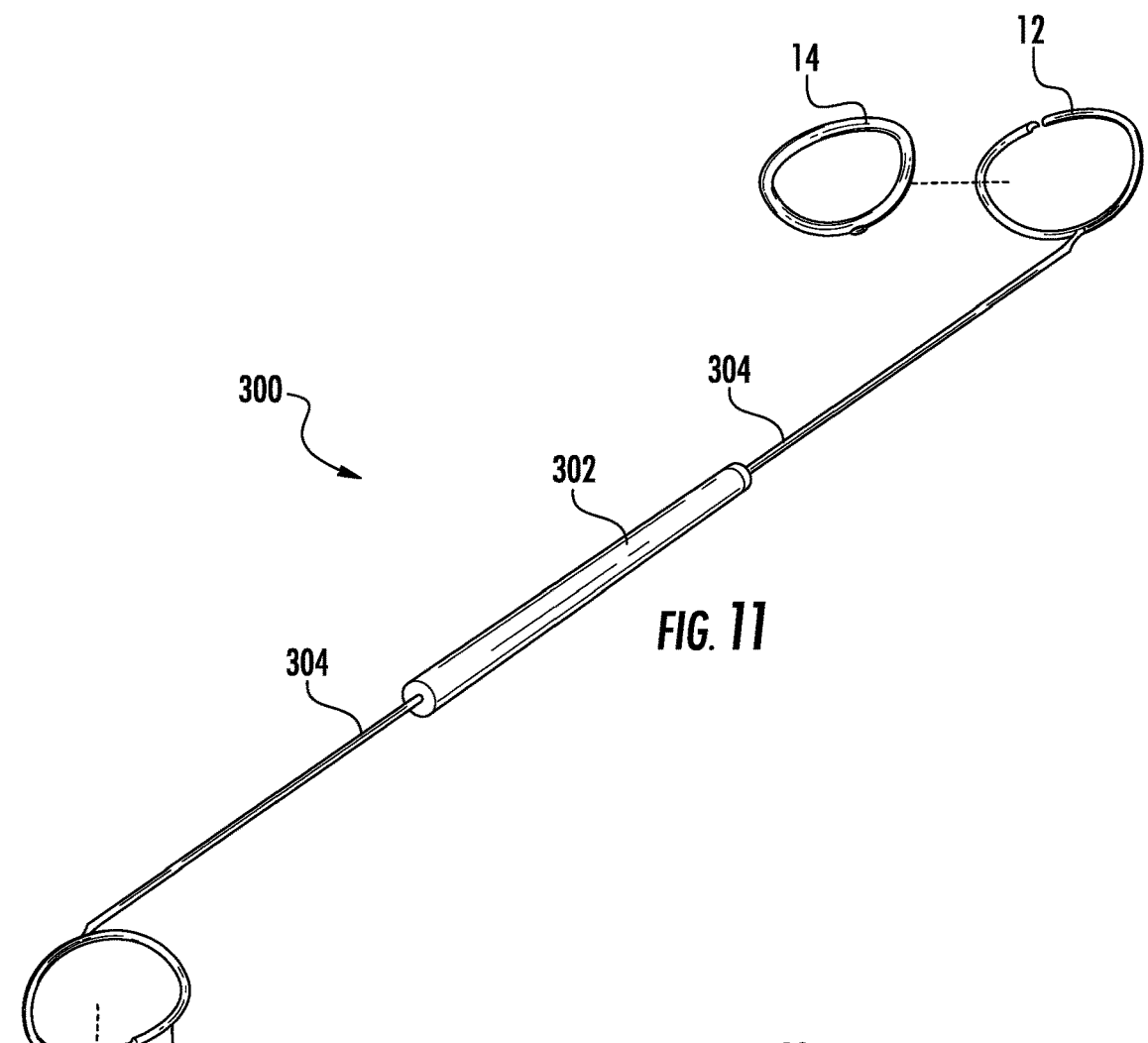
FIG. 11 is a perspective view of a third alternative embodiment of the heart valve ring sizing tool of the present invention that use a handle with a flexible shaft attached to the outer ring with a removable inner ring.
Figure 12:
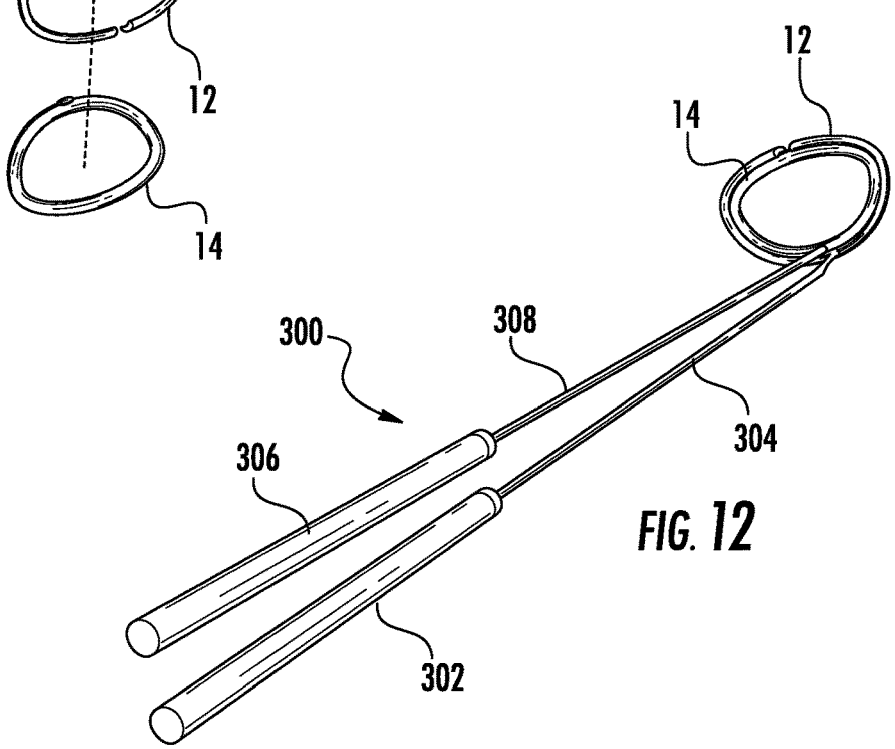
FIG. 12 is a perspective view of a fourth alternative embodiment of the heart valve ring sizing tool of the present invention that uses a handle for each of the inner ring and the outer ring.

Referring to FIG. 11, a third alternative embodiment 300 of the hearts valve sizing tool is shown generally. The tool 300 includes a handle 302 with one or more shafts 304. The shafts 304 may be flexible or rigid. At the end of each shaft 304 is an outer ring 12, each of different and adjacent sizes. Each outer ring 12 has a matching and separable inner ring 14 as described above for the first embodiment 10. The inner ring 14 may be inserted and removed with forceps. The inner rings 14 may also have a handle 306 extending therefrom with a flexible or rigid shaft 308 as well, to remove the need for the use of forceps to insert and remove the inner ring 14 from the outer ring 12 as seen in FIG. 12.

Figure 13:
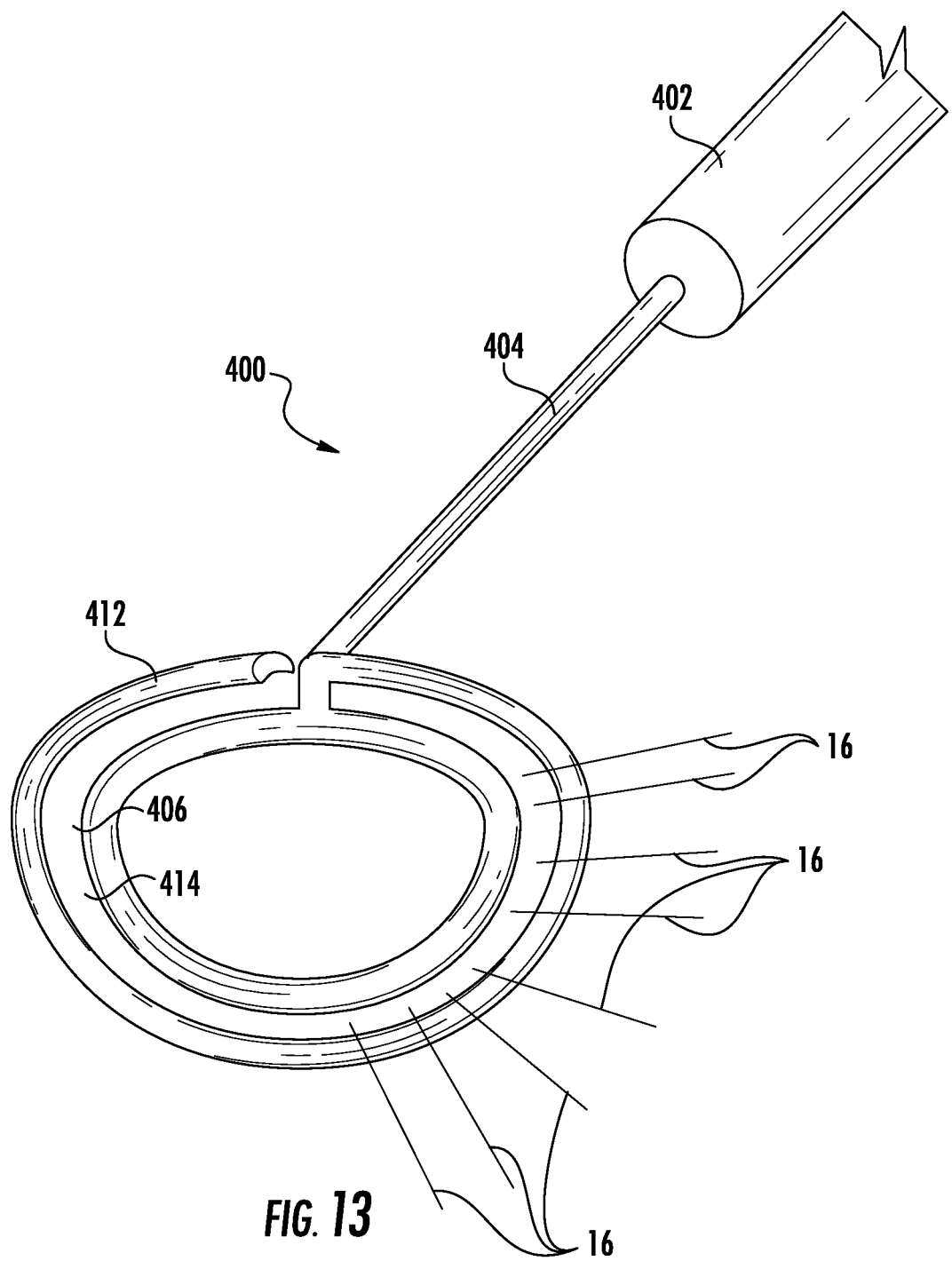
FIG. 13 is a perspective view of a fifth alternative embodiment of the heart valve ring sizing tool of the present invention that includes a unitary inner and outer ring attached to a single handle.

Referring now to FIG. 13, a fifth embodiment 400 could be in the form of a single device on a handle 402 that includes a flexible or rigid shaft 404. Sutures 16 are gathered in a circular motion of the hand within a channel 406 formed between the inner ring 414 and the outer ring 412. The rings 412, 414 are "pushed up against" the valve annulus via the handle 402 for sizing and intraoperative testing of the valve repair. The inner ring 414 and the outer ring 412 may also be hinged together to permit the inner ring 414 to be swung out the way. The handle 402 may be removable also. The hinge mechanism functions in place of snapping the two rings together, as in the other embodiments, and provides ease of gathering sutures 16 while still retaining the quality of gently gripping the sutures 16 as the other embodiments described above.

In all embodiments, access for sutures through the outer ring can be in the form of a simple defect. Possibly one variant would provide for temporary exposure of a defect created by a quick "bending-apart" of the ring which would then "spring-back" into its original shape of what appears to be a complete ring (possibly facilitated by a mechanism to open the device). Alternatively, a small defect can simply remain uncovered, or a small latch can cover the defect, or the outer layer can slide over the defect.

Various mechanisms can be employed to hold the device (via the sutures) firmly up against the annulus. The simplest form may be simple friction provided by a rubber-like coating as described above. Though, other mechanisms/materials may provide a similar function.

It would be appreciated by those skilled in the art that various changes and modifications can be made to the illustrated embodiments without departing from the spirit of the present invention. All such modifications and changes are intended to be within the scope of the present invention.

I claim:

1. A device for measuring heart valve for sizing a heart valve reinforcement ring, comprising:
   a first handle having a first shaft;
   an outer ring coupled to the first shaft, the outer ring having an inner surface; and
   an inner ring having an outer surface, the inner ring removably couplable to the outer ring;
   the inner surface of the outer ring and the outer surface of the inner ring further having reciprocal mating surfaces configured and arranged to grip sutures therebetween when coupled together.

2. The device of claim 1, wherein the outer ring further comprises a defect forming a break in the outer ring.

3. The device of claim 1, wherein the inner surface of the outer ring is concave, and the outer surface of the inner ring is convex.

4. The device of claim 1, wherein the first shaft is flexible.

5. The device of claim 1, wherein the first shaft is bendable.

6. The device of claim 1, wherein the first shaft is detachable from the outer ring.

7. The device of claim 1, further comprising a second handle having a second shaft, wherein the inner ring is connected to the second shaft.

8. The device of claim 7, wherein the second shaft is flexible.

9. The device of claim 7, wherein the second shaft is detachable from the inner ring.

10. The device of claim 1, further comprising a second shaft extending from the first handle, wherein a second outer ring is connected to the second shaft.

11. The device of claim 10, wherein the second shaft is flexible.

12. The device of claim 10, wherein the second shaft is detachable from the second outer ring.

13. A device for measuring heart valve for sizing a heart valve reinforcement ring, comprising:
   a first handle having a first shaft;
   a second handle having a second shaft;
   an outer ring coupled to the first shaft, the outer ring having an inner surface; and
   an inner ring couple to the second shaft, the inner ring having an outer surface, the inner ring removably couplable to the outer ring;
   the inner surface of the outer ring and the outer surface of the inner ring further having reciprocal mating surfaces configured and arranged to grip sutures therebetween when coupled together.

14. The device of claim 13, wherein the outer ring further comprises a defect forming a break in the outer ring.

15. The device of claim 13, wherein the inner surface of the outer ring is concave, and the outer surface of the inner ring is convex.

16. The device of claim 13, wherein the first shaft is flexible.

17. The device of claim 13, wherein the second shaft is flexible.

* * * * *